United States Patent
Schmidt

(10) Patent No.: US 10,977,795 B2
(45) Date of Patent: Apr. 13, 2021

(54) METHOD AND DEVICE FOR DETERMINING A FLOW SITUATION IN A VESSEL

(71) Applicant: Siemens Healthcare GmbH, Erlangen (DE)

(72) Inventor: Sebastian Schmidt, Weisendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 163 days.

(21) Appl. No.: 15/986,859

(22) Filed: May 23, 2018

(65) Prior Publication Data
US 2018/0350074 A1  Dec. 6, 2018

(30) Foreign Application Priority Data
May 30, 2017  (EP) .................... 17173406

(51) Int. Cl.
*G06T 7/00* (2017.01)
*A61B 5/02* (2006.01)
(Continued)

(52) U.S. Cl.
CPC ............ *G06T 7/0016* (2013.01); *A61B 5/021* (2013.01); *A61B 5/02028* (2013.01); *A61B 5/0263* (2013.01); *A61B 6/5217* (2013.01); *A61B 8/5223* (2013.01); *G06T 7/40* (2013.01); *A61B 5/0073* (2013.01); *A61B 5/7267* (2013.01); *A61B 5/743* (2013.01);
(Continued)

(58) Field of Classification Search
CPC ...................... G06T 7/0016; G06T 7/40; G06T 2207/20081; A61B 5/02028; A61B 5/021; A61B 5/0263; A61B 8/5223; A61B 5/0073; A61B 5/7267; A61B 5/743; A61B 2576/02
USPC .......................................................... 382/128
See application file for complete search history.

(56) References Cited

U.S. PATENT DOCUMENTS

| 2017/0071496 | A1* | 3/2017 | Gillies | ................. A61B 5/0263 |
| 2017/0103525 | A1* | 4/2017 | Hu | ........................ G06T 7/0012 |
| 2017/0243364 | A1* | 8/2017 | Carmi | ....................... G06T 7/45 |

OTHER PUBLICATIONS

Rohan et al., Modeling of the contrast-enhanced perfusion test in liver based on the multi-compartment flow in porous media, May 2016, Cornell University Library (Year: 2016).*
(Continued)

*Primary Examiner* — Wednel Cadeau
(74) *Attorney, Agent, or Firm* — Harness, Dickey & Pierce, P.L.C.

(57) ABSTRACT

A method and device for determining a flow situation in a vessel are disclosed. According to an embodiment of the method, a first image data set containing image information relating to the vessel is used and a vascular tree of the vessel is segmented based upon the first image data set. An organ is also segmented based upon the first image data set or of a second image data set and the organ is assigned at least one area of a parenchyma of the organ. Via texture analysis, a texture of the area of the organ is determined and, depending on the texture, the area of the organ is assigned a flow characteristic. Depending on the vascular tree and the flow characteristic assigned to the area of the organ, a value of a measured variable characteristic of the flow situation within the vessel is then determined via a numerical method.

22 Claims, 3 Drawing Sheets

(51) Int. Cl.
  *A61B 5/021* (2006.01)
  *A61B 5/026* (2006.01)
  *A61B 6/00* (2006.01)
  *A61B 8/08* (2006.01)
  *G06T 7/40* (2017.01)
  *A61B 5/00* (2006.01)

(52) U.S. Cl.
  CPC . *A61B 2576/02* (2013.01); *G06T 2207/20081* (2013.01); *G06T 2207/30104* (2013.01)

(56) References Cited

OTHER PUBLICATIONS

Rohan et al., Modeling of the contrast-enhanced perfusion test in liver based on the multi-compartment flow in porous media, May 2016, Cornell University. (Year: 2016).*

Vladimir Lukes et al: "Numerical simulation of liver perfusion: from CT scans to FE model", 7TH European Conference on Python in Science (EUROSCIPY 2014), pp. 79-84, XP055411748, 1; 2014.

Eduard Rohan et al: "Modeling of the contrast-enhanced perfusion test in liver based on the multi-compartment flow in porous median"; Arxiv.org, Cornell University Library, 201 Olin Library Cornell University Ithaca, NY 14853, XP080704439, pp. 1-28; 2016.

German Office Action for Application No. 17173406.4—1657 dated Nov. 22, 2017.

* cited by examiner ately the vessel (i.e. in particular within the tissue region of the
METHOD AND DEVICE FOR DETERMINING A FLOW SITUATION IN A VESSEL

PRIORITY STATEMENT

The present application hereby claims priority under 35 U.S.C. § 119 to European patent application number EP 17173406.4 filed May 30, 2017, the entire contents of which are hereby incorporated herein by reference.

FIELD

At least one embodiment of the invention generally relates to a method which is used to determine a flow situation in a vessel, in particular in a blood vessel. At least one embodiment of the invention also generally relates to a device for determining the flow situation, in particular to carry out at least one embodiment of the method.

BACKGROUND

A flow situation is usually described by different characteristic quantities (parameters) which can be determined for the fluid that is flowing. These characteristic quantities describe in particular the flow resistance within a vessel, the pressure of the fluid (in particular at a specific location in the vessel), a flow rate (also termed volume flow) and/or a flow velocity. In the medical field, determining the flow situation in a blood vessel is often extremely important.

High intravascular pressure, in particular high blood pressure (also known as hypertension), may also be caused by temporary states (e.g. an illness or overexertion) and only be present for a comparatively short time. However, if the high intravascular pressure persists (e.g. in the case of chronic illnesses and/or tissue changes), this can result in damage to the vascular system and/or the heart itself.

To determine in particular a patient's overall blood pressure—more specifically the actual value of the intravascular pressure—the Riva-Rocci method of blood pressure measurement is available as a standard, in particular non-invasive procedure. Here the systolic and diastolic blood pressure value is normally determined on a brachial artery by use of a cuff and stethoscope. The blood pressure determined in this way is usually also termed arterial blood pressure.

However, for many diseases an increased intravascular pressure may only be present locally in regions of the body that are not accessible to the above described blood pressure measurement. Examples of this are so-called pulmonary hypertension (i.e. high blood pressure in the pulmonary circulation) and so-called portal hypertension (i.e. high blood pressure in the portal vein, in particular the portal vein of the liver). Both of these states can be life-threatening for the patient.

In the case of pulmonary hypertension, the flow resistance of the blood vessels of the lung is regularly high e.g. because of changes in the lung tissue, in particular the alveoli. This can result in overloading of the right ventricle of the heart which in the long term may also lead to death. Where applicable, blood clots or the like which increase the flow resistance, for example, can be surgically removed for treatment. Portal hypertension is mainly caused by a change in liver tissue, e.g. cirrhosis. As the body's natural "reaction" to this, blood is partially "diverted" via other vessels (e.g. via the venous system of the esophagus), but this can cause varicose veins to form there which increase the risk of life-threatening (internal) bleeding. Treatment typically involves inserting a so-called portosystemic shunt (a kind of "short circuit") by which blood can be made to bypass the liver and flow into the vena cava.

However, in addition to the above described causes of hypertension, or more specifically for an increased flow resistance within the vessel (e.g. because of liver cirrhosis, pulmonary emphysema, fibrosis of the lung, etc.), that are to be found in the region of the capillaries of the associated vessel (i.e. in particular within the tissue region of the respective organ), in both of the cases described above the increased flow resistance may also be caused by factors within the comparatively larger vessels (e.g. portal vein thrombosis, chronic thromboembolic hypertension, a Budd-Chiari syndrome or similar).

In order to determine the pressure in such regions of the body, specifically vessels, that are inaccessible from outside the body, it is currently generally necessary to employ invasive methods. For example, a catheter is inserted into the vessel in which the intravascular pressure is to be determined. Such a catheter carries a pressure sensor and can therefore in particular directly measure the intravascular pressure locally.

Alternatively, pressure can also be applied to the relevant vessel from outside the vessel via a probe introduce sufficiently close to the vessel—e.g. using a gastroscope-thus enabling the intravascular pressure to be determined locally. However, it is generally recognized that this invariably requires a surgical procedure, which may be undesirable in many cases.

SUMMARY

At least one embodiment of the invention provides an alternative way of determining a flow situation obtaining in a vessel.

At least one embodiment is directed to a method. At least one embodiment is directed to a device. Advantageous and in some cases per se inventive embodiments and further developments of the invention are set forth in the claims and in the following description.

The inventive method of at least one embodiment is used to determine a flow situation in a vessel. According to at least one embodiment of the method, a first image data set containing image information relating to a vessel-preferably a blood vessel—is used. This (first) image data set is preferably generated via a vessel imaging process and made available for carrying out the method. On the basis of the first image data set, a vascular tree—i.e. preferably a local path—of the vessel is then segmented. An organ is also segmented on the basis of the first image data set or a second image data set. The organ is then assigned at least one area of a parenchyma of the organ. A texture of this area of the organ is then determined via texture analysis. Depending on the texture determined, the area of the organ is then assigned a flow characteristic. Depending on the segmented vascular tree and the flow characteristic assigned to the area of the segmented organ, a numerical method is then used to determine at least one value of a measured variable which is characteristic of the flow situation within the vessel. For the vessel (or: "on the vessel") a flow simulation is preferably carried out using the vascular tree of this vessel and the flow characteristic assigned to the area of the organ as information input. As a result of this flow simulation, this at least one value of the characteristic measured variable is then preferably determined.

The device according to at least one embodiment of the invention is used to determine the flow situation in the vessel. For this purpose the device comprises a controller—also termed a processing unit-which is set up and designed to carry out at least one embodiment of the above described method. With particular preference, the device, in particular the controller, has a data transmission link to at least one imaging modality.

The device is optionally in particular the image processing unit of the respective imaging modality itself. Alternatively, the device is connected to at least one network (e.g. a hospital network) in which the above described image data sets are stored.

In at least one embodiment, the controller is designed to segment the vascular tree from the above described first image data set. The controller is also designed to segment the respective organ (in particular the organ to be examined) on the basis of the first image data set or second image data set. In addition, the controller is designed to assign the organ one or more areas of its parenchyma and to carry out texture analysis for each of these areas to determine the respective texture. The controller is also designed to assign the respective area a flow characteristic depending on the texture determined and then, depending on the vascular tree and the respective flow characteristic, to carry out at least one embodiment of the numerical method, i.e. in particular the flow simulation to determine the value of the measured variable characteristic of the flow situation within the vessel.

The device according to at least one embodiment of the invention therefore shares all the advantages of the above described method according to at least one embodiment of the invention.

BRIEF DESCRIPTION OF THE DRAWINGS

Example embodiments of the invention will now be explained in greater detail with reference to a drawing, in which.

Mutually corresponding parts and variables are always provided with the same reference characters in all the figures.

DETAILED DESCRIPTION OF THE EXAMPLE EMBODIMENTS

Figure 1:
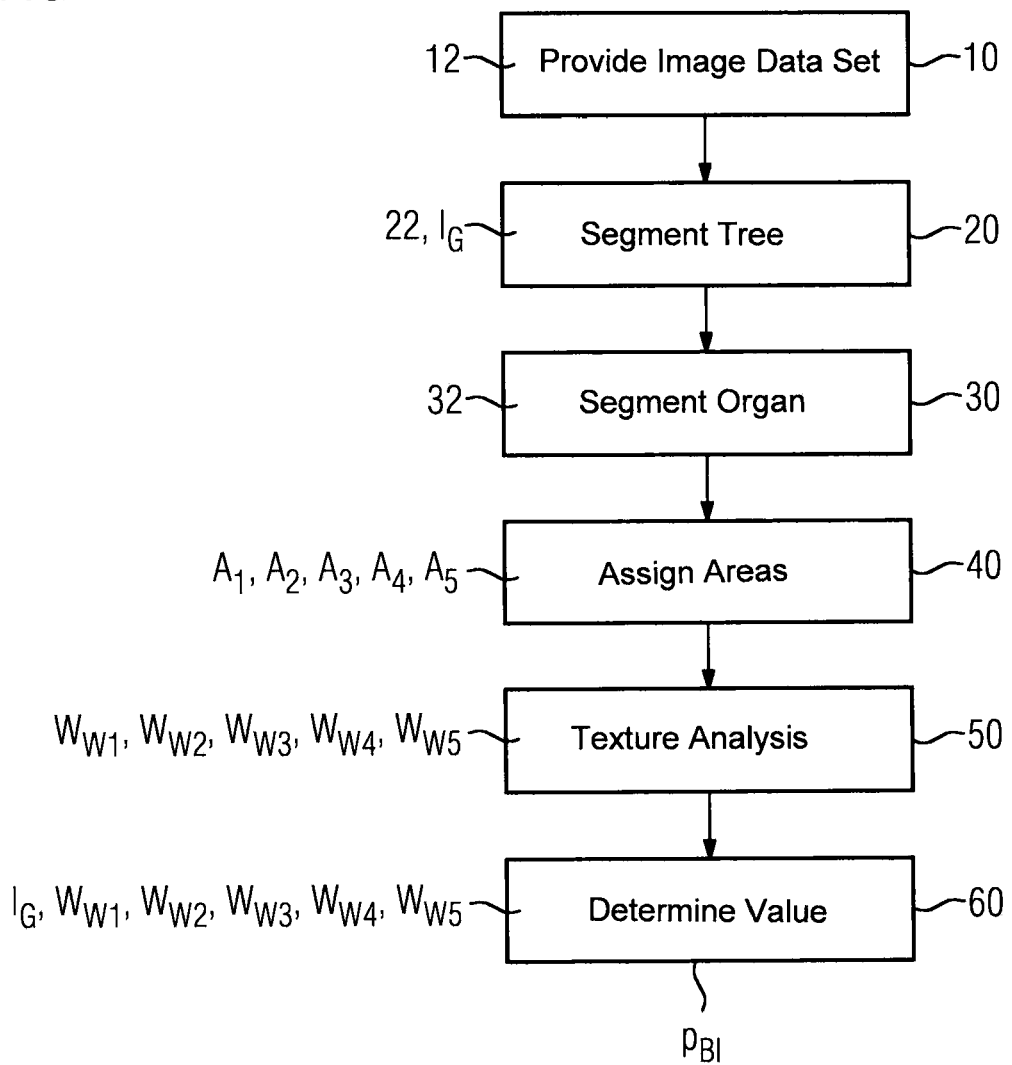
FIG. 1 schematically charts the sequence of a method for determining a flow situation in a vessel.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The inventive method of at least one embodiment is used to determine a flow situation in a vessel. According to at least one embodiment of the method, a first image data set containing image information relating to a vessel-preferably a blood vessel—is used. This (first) image data set is preferably generated via a vessel imaging process and made available for carrying out the method. On the basis of the first image data set, a vascular tree—i.e. preferably a local path—of the vessel is then segmented. An organ is also segmented on the basis of the first image data set or a second image data set. The organ is then assigned at least one area of a parenchyma of the organ. A texture of this area of the organ is then determined via texture analysis. Depending on the texture determined, the area of the organ is then assigned a flow characteristic. Depending on the segmented vascular tree and the flow characteristic assigned to the area of the segmented organ, a numerical method is then used to determine at least one value of a measured variable which is characteristic of the flow situation within the vessel. For the vessel (or: "on the vessel") a flow simulation is preferably carried out using the vascular tree of this vessel and the flow characteristic assigned to the area of the organ as information input. As a result of this flow simulation, this at least one value of the characteristic measured variable is then preferably determined.

The term "segmentation" or "segmenting" is to be understood here and in the following as meaning, in particular, identification of similar regions within the image data set in respect of their image information. Similar regions are preferably to be understood as meaning specific types of tissue, i.e. a vessel and/or an organ, for example. Segmentation preferably involves generating an image or model of the vascular tree (i.e. preferably of the entire vessel contained in the image data set) or "extracting" it from the image data set. Likewise the corresponding segmentation of the organ involves generating its (preferably three-dimensional structure) image or model from the first or possibly second image data set. Sometimes a preferably appropriately assigned data set containing the model of the vessel or organ is present after the relevant segmentation.

The first image data set used for segmentation of the vessel is e.g. an image data set produced using a contrast agent, optionally an image data set produced from such an image data set e.g. via a subtractive method. Depending on the method used for segmentation of the organ, more specifically the segmentation algorithm used, the same first image data set or the in particular different therefrom second image data set (e.g. a native image, an image without administration of contrast agent or similar) is used for segmentation of the organ.

"Characteristic" means here and in the following, in particular, that the measured variable contains quantitative information about the flow situation, more specifically a parameter (or: characteristic quantity) of the flow situation. The measured variable can directly indicate the corresponding parameter of the flow situation. However, the measured variable can also be a variable which is directly or indirectly proportional to the parameter to be indicated. In addition, the measured variable can also have a nonlinear, e.g. logarithmic, exponential or polynomial (i.e. quadratic, cubic, etc.) relationship to the parameter to be indicated.

At least one embodiment of the invention is based on the insight that numerical calculation of the value of the measured variable characteristic of the flow situation within the vessel solely on the basis of the information relating to the vascular tree is subject to unacceptable inaccuracies. This is because the effect of the capillary system of the vessel and/or of the parenchyma of the respective organ that is supplied by the vessel is not taken into account here, as the respective structures thereof (e.g. the diameter of the capillaries) are regularly outside the resolution limit of conventional medical imaging methods. However, it is precisely these regions—i.e. the capillary system or rather the adjacent parenchyma—which regularly differ significantly in respect of their flow characteristics from the vessel regions having resolvable diameters of in particular greater than 10 micrometers.

These regions also have a considerable effect on the flow situation in the larger vessel regions. However, the texture analysis according to the invention advantageously makes it possible to draw inferences about the organ's characteristics actually (i.e. in particular patient-specifically) present within the area of the organ—such as, for example, its density, its tissue composition, its interspersion with capillaries and the like. These characteristics are in turn interrelated with, or at least influence, the flow characteristics within this area of the organ.

Texture analysis now allows the abovementioned inferences also to be drawn for regions having substructures that cannot be resolved further, preferably on the basis of (mathematical or numerical) analyses of minute irregularities within these regions. In particular, the effect of the parenchyma of the organ supplied by the vessel can therefore now also be advantageously taken into account for determining the value of the characteristic measured variable. Because of the texture analysis of the area of the organ, the accuracy for determining the value of the measured variable that can be achieved when assigning the respective flow characteristic to the area of the parenchyma can therefore be significantly increased both inherently and compared to a simple, general assumption of the flow characteristics of the parenchyma in the absence of more precise knowledge of the actual characteristics of the patient-specific parenchyma. Altogether this allows sufficiently precise determination of the flow situation, more specifically of the value of the characteristic measured variable within the vessel, even without surgical intervention in an inaccessible body region.

In an example method variant embodiment, for the vascular tree (preferably as early as the segmentation stage), geometric information about the vascular tree is determined, in particular a local path of a lumen of the vessel—in particular the internal diameter or internal cross-sectional area thereof. That is to say, the model of the vascular tree preferably contains information which expediently reflects the lumen of the vessel for each point in the vascular tree. The numerical method for determining the value of the characteristic measured variable, i.e. in particular the flow simulation, is expediently carried out on the basis of the abovementioned geometric information.

In an example method variant embodiment, an intravascular pressure, in particular a blood pressure, is used as the characteristic measured variable for the flow situation within the vessel. In particular the (preferably local) value of the intravascular pressure is therefore determined via the numerical method, more specifically the flow simulation. A flow velocity or volume flow in particular of the blood flowing within the vessel is also used as the measured variable (additionally or alternatively to the intravascular pressure).

In another example method variant embodiment, a parameter (or characteristic quantity) having the assigned (current) value is used as the flow characteristic assigned to the respective area of the organ. In particular, a flow resistance (and the value thereof), a flow velocity and/or a blood flow (in particular the volume flow of the blood) is used as the assigned flow characteristic in each case. These characteristic quantities are known to influence the flow situation obtaining in the higher-order, larger (in particular resolvable) vessel regions, e.g. the blood pressure, volume flow and similar there.

In an example method variant embodiment, the flow characteristic assigned to the area of the organ for the flow simulation, i.e. for calculating the characteristic measured variable via the numerical method, is set as a boundary condition. This flow characteristic thus constitutes a quantity which represents an in particular invariable characteristic in particular for a region adjacent to the structure taken into account in the flow simulation (here in particular the vascular tree, more specifically the geometric model thereof), specifically an invariable value of a variable characteristic of this property. That is to say, in the flow simulation the flow characteristic determined by texture analysis is invariantly predefined for the parenchyma of the organ.

In another example method variant embodiment, the area (of the organ parenchyma) assigned to the organ comprises a region where the resolution is below the resolution limit for the vessel, in particular for the vascular tree thereof. That is to say, the area of the organ is therefore determined for the particular region of the vascular tree that is below the resolution limit. Texture analysis is therefore also advantageously carried out (and in particular "only") for the regions for which no more branches or capillaries of the vascular tree can be resolved and for which, therefore, also no geometric information for the flow simulations can be determined. These regions, more specifically their assigned flow characteristics after texture analysis, are then incorporated, as described above, in particular as boundary conditions in the above described flow simulation.

In an example method variant embodiment, the parenchyma of the organ is sub-divided in particular into a plurality—i.e. two or more—areas which are preferably supplied by a branch of the vascular tree in each case. In particular, such an area is supplied by an arterial and a venous branch of an (arterial and venous respectively) vessel in each case. Texture analysis is then carried out in particular for each of this plurality of areas. Accordingly, each of the areas is then assigned at least one flow characteristic. Sub-dividing the organ into a plurality of areas advantageously enables the precision of the boundary conditions for the flow situation to be increased. Thus, particularly for organs which may exhibit different tissue characteristics distributed over their entire volume—possibly also due to disease—(which are in particular reflected in the respective texture), the overall precision and resolution of the flow characteristics within the organ and therefore also the precision of the flow simulation itself can be increased via a plurality of flow characteristics which comparatively precisely reflect, for the respective region or rather respective area, the characteristic predominating there. In particular, for flow simulation, each in particular only just resolvable vessel branch can be advantageously assigned the flow characteristic of the adjacent parenchyma area as a (local) boundary condition. However, in an alternative or optionally additional method variant, the entire organ is represented by a single area, and thus the entire organ is assigned a uniform flow characteristic (e.g. a flow resistance for the entire organ). This is expedient, for example, for comparatively small organs and/or organs which regularly have no or only negligible deviations in their textures over the entire organ. In this case it is then advantageously possible to save texture analysis workload.

In another example method variant embodiment, at least the vascular tree and the at least one assigned value of the characteristic measured variable are visually displayed-preferably on a display unit of a modality or device carrying out the method. For example, the respective values of the characteristic measured variable are displayed for different regions of the vascular tree by in particular assigning the respective value to the corresponding region (e.g. via a reference line). In particular, for displaying blood pressure values, a the distribution of the individual blood pressure values over the vascular tree is alternatively, or optionally additionally, displayed in a qualitative manner. The vascular tree is preferably displayed color-coded according to the respective blood pressure value. The colors are preferably assigned to a normal and an overpressure in a traffic-light scheme, e.g. green for normal pressure and red for overpressure. This provides medical staff with a simple and rapid means of identifying regions of the vascular tree in which adverse or even critical blood pressures are present. A low pressure is also optionally assigned a color.

In an example method variant embodiment, the respective flow characteristic is assigned to the organ or the particular area of the organ on the basis of a machine learning process. That is to say, texture analysis is preferably implemented via a "self-learning" analysis algorithm which is in particular "trained" on the basis of empirically determined data. The empirical data used is comparison data, for example, where the blood pressure within a vessel was determined via conventional (in particular invasive) measurement methods. On the basis of these measured values, the respective flow characteristic is assigned to the respective organ area to be analyzed via texture analysis such that the subsequent flow simulation of the vascular tree, or more specifically the result thereof, is approximated to the result actually measured, or preferably made to coincide therewith. By way of such repeated "reverse analyzing", the analysis algorithm is trained as to which flow characteristics are to be assigned to specific textures. Alternatively, as part of texture analysis a "lookup table" in which the empirically determined flow characteristics for already known textures are stored is used to assign the respective flow characteristic. During texture analysis, the textures determined are compared with the already known textures (e.g. using pattern recognition) and the corresponding flow characteristic is read from the table. In another optional variant, for texture analysis a model of the flow characteristics as a function of the texture is implemented. In this case the respective flow characteristics are therefore determined via a numerical method on the basis of the texture.

In another example method variant embodiment, a so-called direct-conversion computed tomography (CT) scanner is used as the imaging modality for generating in particular the first, but also optionally the second image data set. This advantageously has a particularly high resolution, so that even comparatively small vascular branches (i.e. vessels having a comparatively small diameter) can be displayed or resolved. Alternatively, imaging methods such as e.g. (possibly contrast-agent-aided or flow-sensitive) magnetic resonance tomography (MRT), positron emission tomography (PET), (Doppler) ultrasound, angiography and similar can also be used.

Optionally the first image data set is likewise used for texture analysis. However, in an expedient method variant, a second or possibly a third image data set is used for texture analysis. The second or third image data set is optionally provided by the same imaging modality as the first image data set. In this case the second or third image data set is e.g. a native image, i.e. an image or image data set that has not yet been modified by the application of an image data processing algorithm. Alternatively, the second or third image data set is one that has been generated by another imaging modality, i.e. on the basis of an imaging method different from that used for the first image data set. For the case that the second or third image data set is used for texture analysis, this is first made to coincide with the first or second image data set so that the respective area of the organ (determined on the basis of the first or second image data set) is mapped onto the corresponding region of the second or third image data set.

In an example method variant embodiment, additional auxiliary information is also used for determining the value of the characteristic measured variable via the numerical method, i.e. in the flow simulation. This auxiliary information includes, for example, gradients of a contrast agent concentration (time and/or local gradients), so-called time to peak information for contrast agent administration and similar. In addition, patient-specific data such as e.g. size and/or weight of the organ, of the patient, BMI, age, gender, spirometry data, diffusion data, laboratory values (particularly of a blood test) of the patient and similar are also used as auxiliary information. This enables the result of the flow simulation to be improved and/or reduces the computational burden.

In another example method variant embodiment (preferably subsequent to a first simulation pass of the type described above to determine the actual state), the vascular tree and/or the organ or the particular area of the organ is modified. In particular, the respective model—i.e. the local, in particular geometric pattern of the vascular tree or e.g. the structure of the organ—is modified. The modified vascular tree or the modified organ is then taken into account for determining the value of the characteristic measured variable—i.e. for the flow simulation. In particular, depending on the modification of the respective area of the organ, the latter is assigned an (in particular correspondingly modified) flow characteristic. The flow simulation is then carried out in accordance with the modified vascular tree or rather of the respective modified flow characteristic, and the respective value of the characteristic measured variable is determined. This provides an advantageous means of estimating the results of a planned invasive procedure which can (in particular is designed to) produce the abovementioned modification in the vascular tree or organ. In particular, for this purpose a comparison of the simulated flow situations is performed before and after the respective modification. The above mentioned modification is e.g. a planned resection of tissue of the organ and/or of a vascular branch, the insertion of stent in a vessel branch or similar. The above described method can therefore be advantageously used not only for determining the actual state of the flow situation in a vessel but also for planning an invasive surgical procedure, in particular for estimating the result thereof.

The numerical method, i.e. the flow simulation, is based e.g. on approximate solutions for individual sections of the vascular tree which in particular take flow laws such as Hagen-Poiseuille, Bernoulli, etc. into account, on solutions of differential equations (Navier-Stokes, Euler, etc.), on machine learning methods, resistance calculation as per Kirchhoff's laws and similar.

The device according to at least one embodiment of the invention is used to determine the flow situation in the vessel. For this purpose the device comprises a controller—also termed a processing unit—which is set up and designed to carry out at least one embodiment of the above described method. With particular preference, the device, in particular the controller, has a data transmission link to at least one imaging modality.

The device is optionally in particular the image processing unit of the respective imaging modality itself. Alternatively, the device is connected to at least one network (e.g. a hospital network) in which the above described image data sets are stored.

The controller, in at least one embodiment, is designed to segment the vascular tree from the above described first image data set. The controller is also designed to segment the respective organ (in particular the organ to be examined) on the basis of the first image data set or second image data set. In addition, the controller is designed to assign the organ one or more areas of its parenchyma and to carry out texture analysis for each of these areas to determine the respective texture. The controller is also designed to assign the respective area a flow characteristic depending on the texture determined and then, depending on the vascular tree and the respective flow characteristic, to carry out at least one embodiment of the numerical method, i.e. in particular the flow simulation to determine the value of the measured variable characteristic of the flow situation within the vessel.

The device according to at least one embodiment of the invention therefore shares all the advantages of the above described method according to at least one embodiment of the invention.

The conjunction "and/or" is to be understood here and in the following as meaning that the features or terms linked by way of this conjunction may be implemented or occur both jointly and as alternatives to one another.

Figure 2:
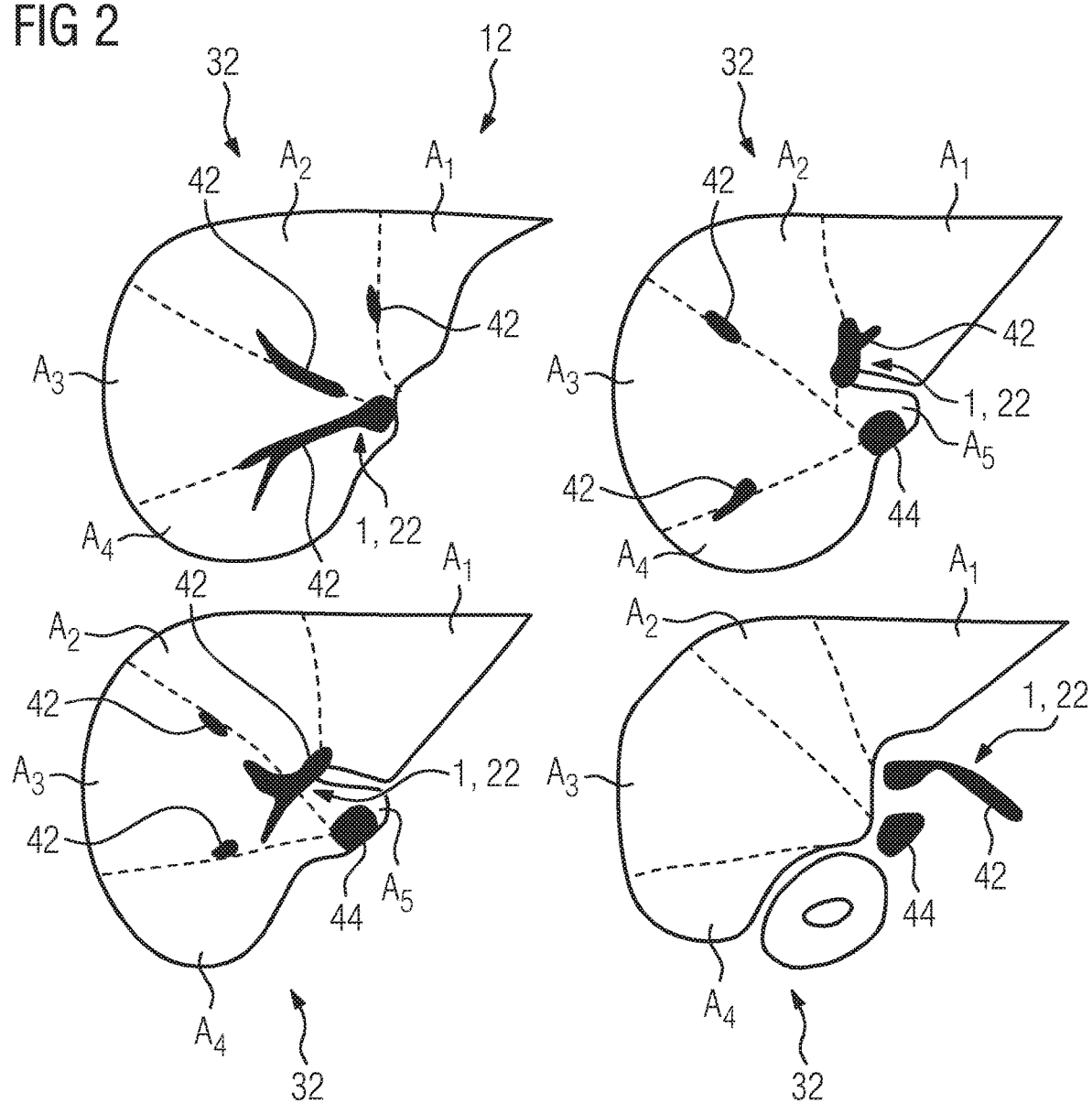
FIG. 2 shows four schematic sectional plan views through an organ, and FIG. 3 schematically illustrates a device for carrying out the method according to FIG. 1.
Figure 3:
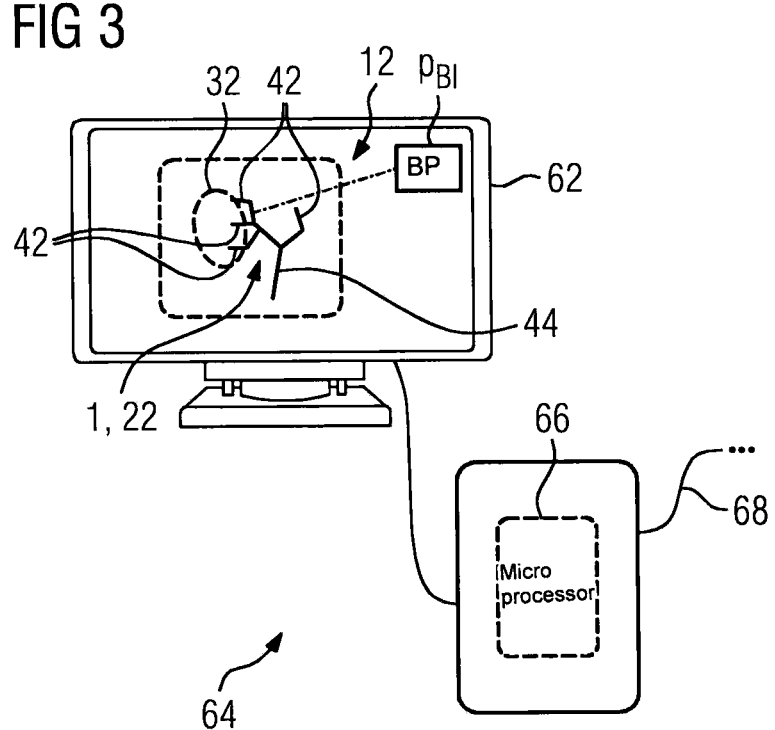

FIG. 1 schematically charts the sequence of a method for determining a flow situation in a vessel 1 (cf. FIG. 2 and FIG. 3). In a first method step 10 a first image data set 12 containing image information for the vessel 1 is provided. Specifically, this first image data set 12 is read from a memory, i.e. loaded. In an optional example embodiment, the first image data set 12 is generated as part of the first method step 10 via an imaging modality, more specifically a CT scanner. In a second method step 20 a vascular tree 22 of the vessel 1 is segmented on the basis of the first image data set 12. The vascular tree 22 represents the local, specifically geometric path of the vessel 1 within the image described by the image data set 12—preferably a volumetric image which is possibly subdivided into a plurality of cross-sectional images (see FIG. 2). As part of segmentation, i.e. of the second method step 20, geometric information IG about the vascular tree 22 is determined. This geometric information IG specifically reflects the local path of a lumen—i.e. the value of the internal diameter or internal cross-sectional area—of the vessel 1 along the vascular tree 22. In a third method step 30, an organ—in this example the liver 32—is segmented on the basis of the first image data set 12. That is to say, in the third method step 30 the portions of the first image data set 12 which map the liver 32 are segmented. A structural image of the organ, i.e. of the liver 32, is produced in a comparable manner to the second method step 20.

For the parenchyma, i.e. for the functional tissue of the liver 32, in a fourth method step 40 a number of areas A1-A5 (cf. FIG. 2) are determined and assigned to the liver 32. In other words the liver 32 is subdivided into these areas A1-A5. Each of these areas is "supplied" by a branch 42 of the vascular tree 22. Each vascular branch 42 represents a section branching off a main section or trunk 44 of the vessel 1.

In a subsequent method step 50, texture analysis is carried out for each area $A_1$-$A_5$, of the liver 32. Specifically, a (mathematical) evaluation of the first image data set 12 is performed for each area $A_1$-$A_5$, by which irregularities within the image region constituting the respective area $A_1$-$A_5$ are detected and the density of the tissue there is analyzed, or more specifically determined. As a result of this texture analysis, each area $A_1$-$A_5$ is assigned a texture. Depending on this texture, each of the areas $A_1$-$A_5$ is assigned a flow characteristic, or more specifically a current value of a flow resistance (hereinafter referred to as resistance value $W_{W1}$-$W_{W5}$).

In a further method step 60, a value of a measured variable characteristic of the flow situation within the vessel 1 is determined. This characteristic measured variable is specifically the blood pressure within the vessel 1. The value determined is referred to here and in the following as the actual blood pressure value $p_{BI}$. To determine the actual blood pressure value $p_{BI}$, as part of method step 60 a numerical method is used, or more specifically a flow simulation is carried out. The flow simulation is carried out for the vascular tree 22—i.e. for the parts of the vessel 1 resolved in the first image data set 12—depending on the geometric information $I_G$. In the flow simulation, the resistance values $W_{W1}$-$W_{W5}$ are used as boundary conditions for the regions of the vascular tree 22 below the resolution limit of the first image data set 12 and for the effect of the parenchyma of the liver 32. Based on the geometric information $I_G$ and the resistance values $W_{W1}$-$W_{W5}$ set as a boundary condition, the flow simulation is carried out by solving Navier-Stokes equations.

In a subsequent method step not shown in greater detail, the actual blood pressure value $p_{BI}$ is displayed for the information of medical staff. Specifically, the actual blood pressure value $p_{BI}$ is indicated on a display device, e.g. a monitor 62 (cf. FIG. 3).

FIG. 3 shows a device for carrying out the method described above. The device is specifically a computer 64 incorporating the monitor 62. In addition, the computer 64 also comprises a controller, or more specifically a microprocessor 66 in which the functionality for carrying out the method described above is implemented as executable software. The computer 64 is connected via a data line 68 to a hospital network in which the image data set 12 is stored in a database. In an optional example embodiment, the computer 64 is directly connected to the imaging modality via the data line 68.

FIG. 3 shows by way of example the result of the flow situation as displayed on the monitor 62. The actual blood pressure value $p_{BI}$ is assigned to a section of the vascular tree 22 via a reference line. Specifically, different sections of the vascular tree 22 are each assigned an actual blood pressure value $p_{BI}$ (not shown in greater detail for reasons of clarity).

In an alternative or, optionally, additionally selectable display variant, the vascular tree 22 is color-coded according to the actual blood pressure value $p_{BI}$ obtaining in each case. Thus, an area in which the actual blood pressure value $p_{BI}$ corresponds to normal pressure is marked green. Another region of the vascular tree 22 in which the actual blood pressure value $p_{BI}$ exceeds normal pressure is marked red, for example, thereby providing a simple means of drawing the attention of medical staff to this region.

In an optional example embodiment not shown in greater detail, the method steps 30, 40 and 50 are carried out on the basis of the second image data set. This second image data set is a native image, for example, from which the first image data set was generated e.g. by a subtractive method. Alternatively, the second image data set is an image data set that was produced via an imaging modality other than the CT scanner used for the first image data set 12.

The subject matter of the invention is not limited to the examples described above. Indeed, further embodiments of the invention will be inferred from the above description by persons skilled in the art. In particular, the individual features described on the basis of the different example embodiments of the invention and the variants thereof can also be combined with one another in other ways.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a flow situation within a vessel, the method comprising:
    obtaining a first image data set including image information relating to the vessel;
    segmenting a vascular tree of the vessel based upon the first image data set;
    segmenting an organ based upon the first image data set or a second image data set;
    assigning the organ at least one area of a parenchyma of the organ;
    determining, via texture analysis, a texture of the at least one area of the organ assigned;
    assigning a flow characteristic, depending on the texture determined, to the at least one area of the organ;
    conducting a flow simulation based on the vascular tree and the assigned flow characteristic; and
    determining, via a numerical method, based on the conducted flow simulation, a value of a measured variable characteristic of the flow situation, said value representing at least one of an actual flow resistance, an actual pressure of a fluid, an actual flow rate, and an actual flow velocity, within the vessel.

2. The method of claim 1, wherein, for the vascular tree, geometric information about the vascular tree is determined, and wherein the numerical method is carried out based upon the geometric information about the vascular tree.

3. The method of claim 1, wherein an intravascular pressure is used as a characteristic measured variable.

4. The method of claim 1, wherein a value of at least one of a flow resistance, of a flow velocity and a blood flow is used as the flow characteristic assigned to the at least one area of the organ.

5. The method of claim 1, wherein the flow characteristic assigned to the at least one area of the organ is used as a boundary condition within the numerical method.

6. The method of claim 1, wherein the at least one area of the organ is determined for a region for which a resolution is below a resolution limit for the vascular tree.

7. The method of claim 1, wherein the vascular tree and the value of the measured variable characteristic, of the flow situation within the vessel, are visually displayed.

8. The method of claim 1, wherein the flow characteristic is assigned to the at least one organ area of the organ based upon a machine learning process.

9. The method of claim 1, wherein a second or third image data set is used for texture analysis.

10. The method of claim 1, wherein additional auxiliary information is used to determine the value of the measured variable characteristic.

11. The method of claim 1, wherein at least one of the vascular tree and the at least one area of the organ is modified and wherein the value of the measured variable characteristic is determined according to the vascular tree modified and the flow characteristic assigned to the at least one area of the organ modified.

12. A non-transitory machine-readable data carrier including program code for carrying out the method of claim 1 when the program code is run on a computer.

13. The method of claim 1, further comprising predicting an actual blood pressure value within the vessel.

14. The method of claim 2, wherein the geometric information about the vascular tree includes geometric information about a local path of a lumen of the vessel.

15. The method of claim 2, wherein the at least one area of the organ is determined for a region for which a resolution is below a resolution limit for the vascular tree.

16. The method of claim 2, wherein the vascular tree and the value of the measured variable characteristic, of the flow situation within the vessel, are visually displayed.

17. The method of claim 3, wherein the intravascular pressure is a blood pressure.

18. The method of claim 6, wherein the parenchyma of the organ is sub-divided into a plurality of areas, and wherein texture analysis is carried out only for the region for which resolution is below the resolution limit.

19. A device for determining a flow situation in a vessel, comprising:
a controller, designed to
obtain a first image data set including image information relating to the vessel,
segment a vascular tree of the vessel based upon the first image data set,
segment an organ based upon the first image data set or a second image data set,
assign the organ at least one area of a parenchyma of the organ,
determine, via texture analysis, a texture of the at least one area of the organ,
assign a flow characteristic, depending on the texture determined, to the at least one area of the organ,
conduct a flow simulation based on the vascular tree and the assigned flow characteristic, and
determine, via a numerical method, based on the conducted flow simulation, a value of a measured variable characteristic of the flow situation, said value representing at least one of an actual flow resistance, an actual pressure of a fluid, an actual flow rate, and an actual flow velocity, within the vessel.

20. An imaging modality, comprising the device of claim 19.

21. A device for determining a flow situation in a vessel, comprising:
a memory storing program computer-readable instructions; and
one or more processors configured to execute the computer-readable instructions such that the one or more processors are configured to,
obtain a first image data set including image information relating to the vessel,
segment a vascular tree of the vessel based upon the first image data set,
segment an organ based upon the first image data set or a second image data set,
assign the organ at least one area of a parenchyma of the organ,
determine, via texture analysis, a texture of the at least one area of the organ,
assign a flow characteristic, depending on the texture determined, to the at least one area of the organ,
conduct a flow simulation based on the vascular tree and the assigned flow characteristic, and
determine, via a numerical method, depending on the conducted flow simulation, a value of a measured variable characteristic of the flow situation, said value representing at least one of an actual flow resistance, an actual pressure of a fluid, an actual flow rate, and an actual flow velocity, within the vessel.

22. An imaging modality, comprising the device of claim 21.

* * * * *